(12) United States Patent
Rice et al.

(10) Patent No.: US 7,663,664 B2
(45) Date of Patent: Feb. 16, 2010

(54) ABSOLUTE INTENSITY DETERMINATION FOR A FLUORESCENT LIGHT SOURCE IN LOW LEVEL LIGHT IMAGING SYSTEMS

(75) Inventors: Bradley Rice, Danville, CA (US); Michael D. Cable, Danville, CA (US)

(73) Assignee: Xenogen Corporation, Alameda, CA (US)

( * ) Notice: Subject to any disclaimer, the term of this patent is extended or adjusted under 35 U.S.C. 154(b) by 382 days.

(21) Appl. No.: 11/523,480

(22) Filed: Sep. 18, 2006

(65) Prior Publication Data
US 2007/0013780 A1 Jan. 18, 2007

(51) Int. Cl.
*H04N 17/00* (2006.01)
*G06K 9/00* (2006.01)

(52) U.S. Cl. .................. 348/187; 382/162; 382/167
(58) Field of Classification Search ......... 348/187–194, 348/180, 181, 184, 185; 382/162, 167
See application file for complete search history.

(56) References Cited

U.S. PATENT DOCUMENTS

| | | |
|---|---|---|
| 4,196,994 A | 4/1980 | De Jesus et al. |
| 4,727,247 A * | 2/1988 | Johnston ............... 250/361 R |
| 4,948,975 A | 8/1990 | Erwin et al. |
| 5,008,548 A | 4/1991 | Gat |
| 5,060,061 A | 10/1991 | Shishido et al. |
| RE33,973 E | 6/1992 | Kriz et al. |
| 5,130,794 A | 7/1992 | Ritchey |
| 5,202,091 A | 4/1993 | Lisenbee |
| 5,227,627 A | 7/1993 | Gamarnik et al. |
| 5,272,518 A | 12/1993 | Vincent |
| 5,319,209 A | 6/1994 | Miyakawa et al. |
| 5,376,803 A | 12/1994 | Mc Fee et al. |
| 5,414,258 A | 5/1995 | Liang |

(Continued)

FOREIGN PATENT DOCUMENTS

EP   0 228 877   7/1987

(Continued)

OTHER PUBLICATIONS

Mahmood, U. et al., "Near-Infrared Optical Imaging of Protease Activity for Tumor Detection", Radiology 1999, 213, pp. 866-870.

(Continued)

*Primary Examiner*—Paulos M Natnael
(74) *Attorney, Agent, or Firm*—Beyer Law Group LLP

(57) ABSTRACT

The invention describes systems and methods to obtain and present imaging data in absolute units. The systems and methods convert relative image data produced by a camera to absolute light intensity data using a compensation factor. The compensation factor accommodates for hardware and specific imaging conditions in the imaging system that variably affect camera output. The present invention determines the compensation factor based on assessing the output of the camera against a known light source for a specific set of imaging conditions in the imaging system. The compensation factor is then stored in memory corresponding to the specific set of imaging conditions. Upon subsequent imaging with the set of imaging conditions, the corresponding compensation factor is called from memory and applied to the camera output. A compensation factor may be determined and stored for each hardware state and imaging condition available to the imaging system.

19 Claims, 9 Drawing Sheets

U.S. PATENT DOCUMENTS

| | | | |
|---|---|---|---|
| 5,515,161 | A | 5/1996 | Blumenfeld |
| 5,587,583 | A | 12/1996 | Chin et al. |
| 5,636,299 | A | 6/1997 | Bueno et al. |
| 5,637,874 | A | 6/1997 | Honzawa et al. |
| 5,650,135 | A | 7/1997 | Contag et al. |
| 5,672,881 | A | 9/1997 | Striepeke et al. |
| 5,689,110 | A * | 11/1997 | Dietz et al. ............. 250/252.1 |
| 5,705,807 | A | 1/1998 | Throngnumchai et al. |
| 5,738,101 | A | 4/1998 | Sappey |
| 5,796,477 | A | 8/1998 | Teich et al. |
| 5,840,572 | A | 11/1998 | Copeland et al. |
| 5,865,754 | A | 2/1999 | Sevick-Muraca et al. |
| 5,867,250 | A | 2/1999 | Baron |
| 5,883,830 | A * | 3/1999 | Hirt et al. ............. 365/185.03 |
| 5,970,164 | A | 10/1999 | Bamberger et al. |
| 6,205,244 | B1 * | 3/2001 | Bawolek et al. ............ 382/162 |
| 6,217,847 | B1 | 4/2001 | Contag et al. |
| 6,242,743 | B1 | 6/2001 | DeVito et al. |
| 6,321,111 | B1 | 11/2001 | Perelman et al. |
| 6,364,829 | B1 | 4/2002 | Fulghum |
| 6,381,058 | B2 | 4/2002 | Ramm et al. |
| 6,597,439 | B1 * | 7/2003 | Hakamata .................... 356/73 |
| 6,615,063 | B1 | 9/2003 | Ntziachristos et al. |
| 6,642,953 | B1 | 11/2003 | Nieto Velasco et al. |
| 6,759,814 | B2 | 7/2004 | Vogel et al. |
| 6,775,567 | B2 | 8/2004 | Cable et al. |
| 6,919,919 | B2 | 7/2005 | Nelson et al. |
| 6,922,246 | B2 | 7/2005 | Nilson |
| 7,116,354 | B2 * | 10/2006 | Rice et al. ................... 348/187 |
| 7,129,464 | B2 | 10/2006 | Buchin |
| 7,151,252 | B2 | 12/2006 | Lehmann et al. |
| 7,331,673 | B2 * | 2/2008 | Ono ........................... 351/221 |
| 7,352,840 | B1 | 4/2008 | Nagarkar et al. |
| 7,482,167 | B2 * | 1/2009 | Sammak et al. ............. 436/164 |
| 2001/0028510 | A1 | 10/2001 | Ramm et al. |
| 2002/0072677 | A1 | 6/2002 | Sevick-Muraca et al. |
| 2003/0036860 | A1 | 2/2003 | Rice et al. |
| 2003/0156194 | A1 | 8/2003 | Sugiura et al. |
| 2005/0077459 | A1 | 4/2005 | Engler et al. |
| 2005/0145786 | A1 | 7/2005 | Rice et al. |
| 2006/0081770 | A1 | 4/2006 | Buchin |

FOREIGN PATENT DOCUMENTS

| | | |
|---|---|---|
| EP | 0 491 131 | 6/1992 |
| EP | 0656731 | 6/1995 |
| FR | 2 802 009 | 6/2001 |
| WO | WO 94/00742 | 1/1994 |
| WO | WO 00/17643 | 3/2000 |

OTHER PUBLICATIONS

Weissleder, R. et al., "Shedding Light onto Live Molecular Targets", Nature Medicine, Jan. 2003, vol. 9, No. 1, pp. 123-128.

Integrated Photomatrix Limited, "Closed Loop Control," Dorset, England, available Dec. 1, 2001.

Dynex Technologies, Inc. website, A Thermo BioAnalysis Company "Dynex Microplates," http://www.dynextechnologies.com/index.html, printed Apr. 19, 2002.

Optronic Laboratories, Inc. website, Manufacturer of Light Measurement Instrumentation, Standards, http://olinet.com/, printed Apr. 19, 2002.

Labsphere website, http://labsphere.com, printed Apr. 19, 2002.

Lambda Research Corporation website, http://lambdares.com, printed Apr. 19, 2002.

Hamamatsu Coporation USA website, http://usa.hamamatsu.com/ pp. 1-4, Apr. 27, 2001, printed on Apr. 27, 2001.

Hamamatsu, Imaging Box Instruction Manual, 55310-224-1, Nov. 2000.

Prahl, Scott. "Optical Phantoms," http://omlc.ogi.edu/classroom/phantom/index.html, 1998, printed Jul. 18, 2007.

Vernon, Marcia L. et al., "Fabrication and characterization of a solid polyurethane phantom for optical imaging through scattering media," Applied Optics, vol. 38, No. 19, Jul. 1, 1999, pp. 4247-4251.

European Search Report dated Feb. 5, 2008 from EP Application No. 02742268.2 (5 pages).

Office action dated Dec. 29, 2008 in U.S. Appl. No. 11/682,710.

Office Action dated Jun. 30, 2009 in U.S. Appl. No. 11/682,710.

Notice of Allowance dated Oct. 8, 2009 in U.S. Appl. No. 10/997,324.

Summons to Attend Oral Proceedings dated May 8, 2009 for European Application No. 02742268.2.

International Search Report dated May 28, 2009 in PCT Application No. PCT/US08/55965.

Written Opinion dated May 28, 2009 in PCT Application No. PCT/US08/55965.

Notice of Allowance dated Oct. 28, 2009 in U.S. Appl. No. 11/682,710.

* cited by examiner

ABSOLUTE INTENSITY DETERMINATION FOR A FLUORESCENT LIGHT SOURCE IN LOW LEVEL LIGHT IMAGING SYSTEMS

CROSS-REFERENCE TO RELATED APPLICATIONS

This application claims priority under U.S.C. §120 from co-pending U.S. patent application Ser. No. 10/177,647, filed Jun. 20, 2002 and entitled, "ABSOLUTE INTENSITY DETERMINATION FOR A LIGHT SOURCE IN A LOW LEVEL LIGHT IMAGING SYSTEMS", which is incorporated herein for all purposes and which claimed priority under 35 U.S.C. §119(e) from U.S. Provisional Patent Application No. 60/299,685 filed on Jun. 20, 2001, which is incorporated by reference for all purposes; and which was a continuation-in-part of U.S. patent application entitled "Light Calibration Device for Use in Low Level Light Imaging Systems" by Nelson et al., filed on Feb. 6, 2002 (U.S. Pat. No. 6,919,919), which is incorporated by reference herein for all purposes.

FIELD OF THE INVENTION

The present invention relates generally to imaging. In particular, the present invention relates to systems and methods for obtaining the absolute intensity of a light source which is particularly useful in imaging and research applications.

BACKGROUND OF THE INVENTION

One new and specialized type of imaging involves the capture of low intensity light—often on the order of only tens to hundreds of photons—from a light emitting sample. The source of the light indicates portions of the sample, such as traced molecules in a particular portion of a laboratory mammal, where an activity of interest may be taking place. For example, specialized in-vivo imaging applications may include analysis of one or more representations of emissions from internal portions of a specimen superimposed on a photographic representation of the specimen.

Digital cameras used in these imaging systems output image data in "analog digitizer units" (ADU) or "counts". Counts are an arbitrary unit produced by the camera based on the amount of light it receives. The camera includes an array of pixels, each of which converts photons to electrons and generates digital output relative to the number of photons incident on the pixel. A digitizer detects the number of counts produced by the pixels and may add a gain to produce a more suitable output signal. Data from the camera thus comprises a digitized number of counts that is proportional to the number of photons incident on the pixels.

Counts are not an absolute indication of light activity for the light source. Imaging conditions and hardware used in the imaging system for a particular image affect count output. For example, hardware features such as a filter, an iris, f-stop, or position of the light source all affect the number of photons received by the camera, and thus the number of counts output by the camera. In addition, different camera designs may also affect data output. For example, camera output may be altered by a gain that turns pixel output into a more suitable number, which may vary from camera to camera. Counts are thus relative units that refer to the amplitude of a signal output by the camera.

A problem with using counts as a basis for imaging data analysis is that imaging data may only be analyzed or compared locally within a system, and often under identical imaging conditions. It is often desirable to compare imaging data taken under different imaging conditions (e.g. with a different lens) or with different imaging systems (e.g., imaging systems in different locations or using different hardware). Such imaging systems are not currently available. In view of the foregoing, techniques for obtaining absolute imaging data in a low-level light imaging system would be desirable.

SUMMARY OF THE INVENTION

The present invention relates to systems and methods to obtain and present imaging data in absolute light intensity units. The systems and methods convert relative image data produced by a camera to absolute light intensity data using a compensation factor. The compensation factor accommodates for hardware and specific imaging conditions in the imaging system that variably affect camera output. The present invention determines the compensation factor based on assessing the output of the camera against a known light source for a specific set of imaging conditions in the imaging system. The compensation factor is then stored in memory corresponding to the specific set of imaging conditions. Upon subsequent imaging with the set of imaging conditions, the corresponding compensation factor is called from memory and applied to the camera output. A compensation factor may be determined and stored for each hardware state and imaging condition available to the imaging system.

In one aspect, the present invention relates to a method for generating absolute light intensity data for a light source being imaged at low intensity light levels. The method comprises determining a compensation factor for converting data output by a camera into absolute intensity light data, the compensation factor corresponding to a set of imaging conditions. The compensation factor corresponds to a set of imaging conditions. The method also comprises storing the compensation factor. The method further comprises calling the compensation factor based on the set of imaging conditions when the set of imaging conditions are used in imaging the light source. The method additionally comprises modifying image data, output by the camera, by the compensation factor to obtain the absolute light intensity data for the light source.

In another aspect, the present invention relates to a method for imaging a light source at low intensity light levels in an imaging system including a camera and an imaging box. The method comprises setting one or more image capture conditions in the imaging system. The method also comprises capturing luminescent image data from the light source using the camera. The method further comprises converting image data produced by the camera to absolute light data for the light source using a compensation factor that accommodates for differences between the light emitted from the sample and data output by the camera based on a set of imaging conditions.

In yet another aspect, the present invention relates to an imaging system for capturing an image of a light source with a camera. The imaging system comprises an imaging box having a set of walls enclosing an interior cavity. The imaging system also comprises a camera mount configured to position the camera relative to a fixed datum on one of said walls for viewing of the light source by the camera. The imaging system further comprises a processor designed or configured to modify image data produced by the camera to absolute light data for the light source using a compensation factor, based on a set of imaging conditions, that accommodates for differences between the light emitted from the sample and data output by the camera.

In still another aspect, the present invention relates to a computer readable medium including instructions for generating absolute light intensity data for a light source being imaged at low intensity light levels. The instructions comprise instructions for determining a compensation factor for converting data output by a camera into absolute intensity light data, the compensation factor corresponding to a set of imaging conditions. The instructions also comprise instructions for storing the compensation factor. The instructions further comprise instructions for calling the compensation factor based on the set of imaging conditions when the set of imaging conditions are used in imaging the light source. The instructions additionally comprise instructions for modifying image data, output by the camera, by the compensation factor to obtain the absolute light intensity data for the light source.

In another aspect, the present invention relates to systems and methods for calibrating a low-level light imaging system. Techniques described herein employ a light calibration device that is placed within a low level light imaging box to calibrate the system and its constituent imaging components such as the camera, imaging box and lens. The calibration device comprises an array of low-emission light supplies having a known emission. In one embodiment, the array of low-emission light supplies are Lambertian surface emitters with a surface radiance of between about $10^3$ to about $10^{10}$ photons/second/centimeter squared/steradian. By taking an exposure of one or more of the low-power light sources, and comparing the processed result with the known emission, the accuracy of the imaging system and its absolute imaging characteristics may be assessed and verified.

In still another aspect, the present invention relates to a calibration device for calibrating an imaging system. The imaging system is responsible for capturing an image of a low intensity light source. The device comprises an array of low intensity light supplies for emitting light in the range of about $10^3$ to about $10^{10}$ photons/second/centimeter squared/steradian. Each low intensity light supply comprises a light interface for receiving light from a light source and to emit at least a portion of the light from the device. The device also comprises a housing that contains the array of low intensity light supplies. The device further comprises a voltage source, in electrical communication with the light source for each low intensity light supply, and designed or configured to provide power to the light source.

In yet another aspect, the present invention relates to a system for capturing an image of a low intensity light source with a camera. The system comprises an imaging box having a set of walls enclosing an interior cavity and a camera mount configured to position the camera relative the interior cavity. The system further comprises a calibration device including a voltage source and an array of low intensity light supplies. The low intensity light supplies may emit light in the range of about $10^3$ to about $10^{10}$ photons/second/centimeter squared/steradian. Each low intensity light supply comprises a light interface for receiving light from a light source and to emit at least a portion of the light from the device. The voltage source is in electrical communication with the light source for each low intensity light supply. The system additionally comprises a processor designed or configured to receive image data corresponding to light emitted from the calibration device and compare the image data to known light emission data for the calibration device.

In another aspect, the present invention relates to a method for calibrating a system capable of capturing an image of a low intensity light source. The system comprises an imaging box and a camera for capturing the image. The method comprises placing a light calibration device in the imaging box, the light calibration device including an array of low intensity light supplies. The method also comprises emitting light from one or more of the low intensity light supplies in the range of about $10^3$ to about $10^{10}$ photons/second/centimeter squared/steradian. The method further comprises receiving the light from the one or more of the low intensity light supplies using the camera. The method additionally comprises comparing the received light with a known light emission for the one or more of the low intensity light supplies.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

Overview

The present invention converts "relative" units produced by a camera to "absolute" physical units. A distinction between "absolute" physical units and "relative" units as discussed herein is that absolute units refer to light emission data from the source or sample itself, as opposed to counts which refers to light emission incident on a detector—or another relative camera data unit output from a camera component. Regardless of imaging conditions, measurements in absolute units produced by techniques described herein have already taken into account imaging system components, conditions and settings such as integration time, binning, f/stop, and field-of-view. In one embodiment, the absolute units are provided as radiance. For example, systems and methods as described herein may automatically convert relative camera output to photons/second/centimeter squared/steradian where steradian refers to a unit measure of solid angle. These are units of photon radiance on the surface of the sample.

As a result of the techniques described herein, if a user were to take several images (during a single session) of a light source, such as a portion of interest within a mouse, with different integration times or different fields-of-view, the displayed images would all have the same signal amplitude because the radiance on the surface of the animal is not changing—only the camera settings are changing. Basically, the camera settings and other imaging system variables have been compensated out by a compensation factor stored in software that adjusts camera output based on the specific camera settings and other imaging system conditions employed in obtaining the image data.

An advantage of this compensation to a user is that camera settings can now be changed during the course of an experiment without compromising absolute light intensity data integrity. The other advantage of absolute physical units is that images or image data can now be compared quantitatively between different image systems, such as those that employ different cameras and systems at different facilities.

Exemplary Imaging System

Figure 1:
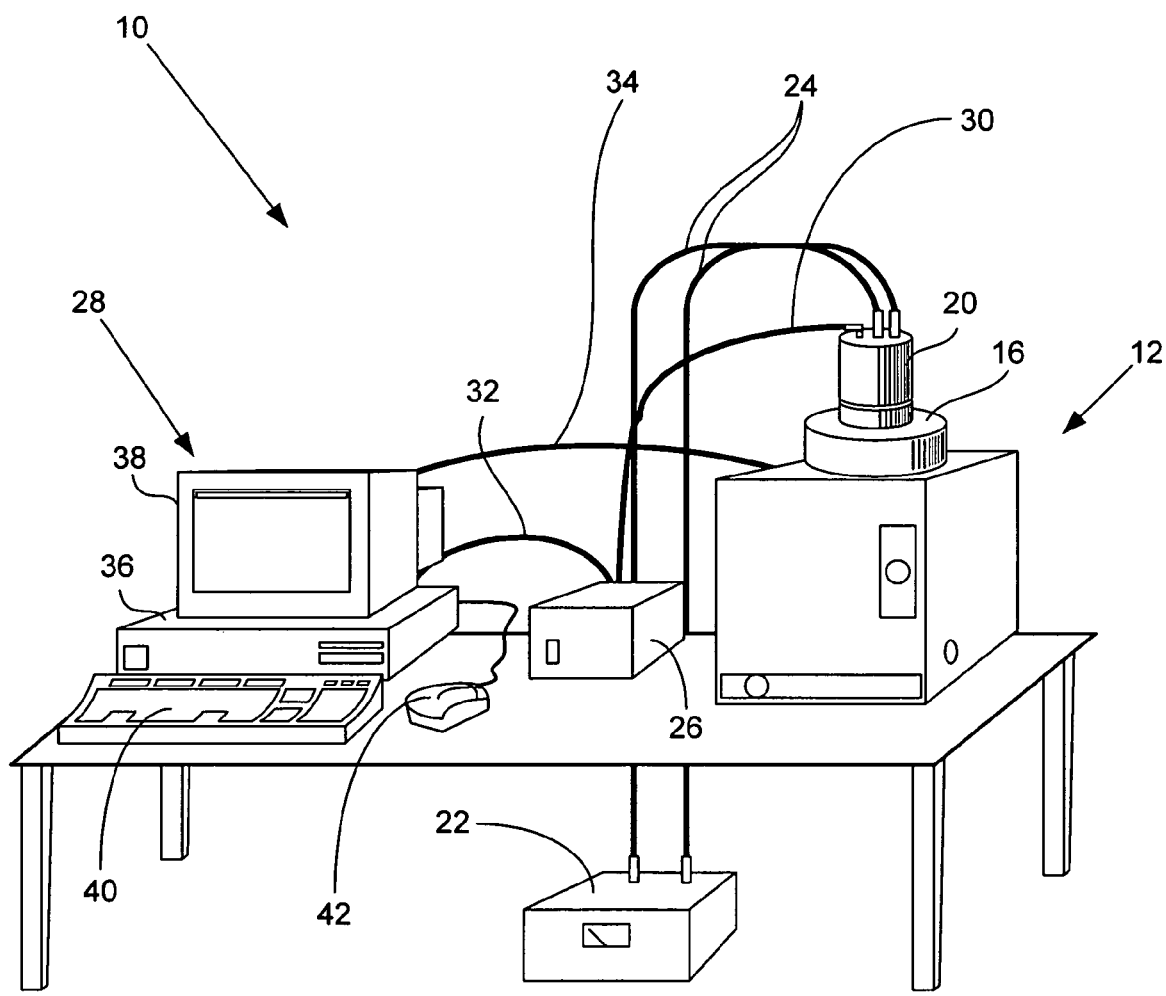
FIG. 1 is a perspective view of an imaging system in accordance with one embodiment of the present invention.

In one aspect, the present invention relates to imaging systems for capturing an image of a low intensity light source. FIG. 1 illustrates an exemplary imaging system 10 configured to capture photographic and luminescence images in accordance with one embodiment of the present invention. Imaging system 10 may be used for imaging a low intensity light source, such as luminescence from luciferase-expressing cells, fluorescence from fluorescing molecules, and the like. The low intensity light source may be emitted from any of a variety of light-emitting samples which may include, for example, tissue culture plates, multi-well plates (including 96, 384 and 864 well plates), and animals or plants containing light-emitting molecules, such as various mammalian subjects such as mice containing luciferase expressing cells.

Imaging system 10 comprises an imaging box 12 having a door and walls that define an interior cavity that is adapted to receive a light-emitting sample in which low intensity light, e.g., luciferase-based luminescence, is to be detected. The calibration device of FIG. 4 may also be placed within box 12. Imaging box 12 is suitable for imaging including the capture of low intensity light on the order of individual photons, for example. Imaging box 12 is often referred to as "light-tight", e.g., it seals out essentially all of the external light from the ambient room from entering the box 12, and may include one or more seals that prevent light passage into the box when the door is closed.

Imaging box 12 includes an upper housing 16 adapted to receive a camera. A high sensitivity camera 20, e.g., an intensified or a charge-coupled device (CCD) camera, is mounted on top of upper housing 16 and positioned above imaging box 12. The CCD camera 20 is capable of capturing luminescent and photographic (i.e., reflection based) images of a sample or calibration device placed within imaging box 12. The CCD camera 20 is cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other methods, such as liquid nitrogen, may be used to cool the CCD camera 20.

An image processing unit 26 optionally interfaces between camera 20 and a computer 28 through cables 30 and 32 respectively. Computer 28, which may be of any suitable type, typically comprises a main unit 36 that typically contains hardware including a processor, memory components such as random-access memory (RAM) and read-only memory (ROM), and disk drive components (e.g., hard drive, CD, floppy drive, etc.). Computer 28 also includes a display 38 and input devices such as a keyboard 40 and mouse 42. Computer 28 is in communication with various components in imaging box 12 via cable 34. To provide communication and control for these components, computer 28 includes suitable processing hardware and software configured to provide output for controlling any of the devices in imaging box 12. The processing hardware and software may include an I/O card, control logic for controlling any of the components of imaging system 10, and a suitable graphical user interface that facilitates user interaction with imaging system 10. Components controlled by computer 28 may include camera 20, the motors responsible for camera 20 focus, the motors responsible for position control of a moveable platform supporting the sample, the camera lens, f-stop, etc.

Computer 28 also includes suitable processing hardware and software for image processing and data manipulation as described herein. For example, a processor within computer 28 may cooperate with stored software that stores compensation factors in a look-up table. In addition, the processor may be configured to access the look-up table based on imaging conditions used in imaging system 10. Further description on many of the processor and software functions for computer 28 will be described in further detail below.

The present invention may be used for a wide variety of imaging applications. Generally, the present invention may be used with systems that employ any non-invasive methods and compositions for detecting, localizing and tracking light-emitting entities and biological events in a mammalian subject. For example, the imaging system 10 of FIG. 1 and compensation techniques described herein may be implemented with intensified Charge-Coupled Device (CCD) cameras to detect the localization of light-producing cells (e.g., certain bacteria or tumor cells made bioluminescent by transforming them with luciferase DNA constructs) inside of living animals, such as mice. In such applications, an animal containing the bioluminescent cells is placed inside of the specimen chamber, and within the field of a photodetection device, such as an intensified CCD camera. The camera is then activated to detect the emitted photons. The photon signal may then be used to construct a luminescent image of photon emission. The luminescent image is constructed without using light sources other than the luminescence from the sample itself. This luminescence is recorded as a function of position to produce the luminescence image. The photographic image may also be taken of the same sample to aid in position visualization of the luminescent image. One approach to generating such composite photographic/luminescence images is described in U.S. Pat. No. 5,650,135 issued to Contag et al. on Jul. 22, 1997. The entire disclosure of that patent is incorporated herein by reference for all purposes.

As the term is used herein, a low intensity light of the present invention refers to light less than about $10^{10}$ photons/second/centimeter squared/steradian. In some cases, the present invention is practiced in the range of about $10^3$ to about $10^{10}$ photons/second/centimeter squared/steradian. For some imaging systems, a low intensity light supply that emits light in the range of about $10^5$ to about $10^7$ photons/second/centimeter squared/steradian is suitable for determining compensation factors as described below.

Relative and Absolute Light Intensity Data Conversion

The present invention converts relative image data produced by a camera to absolute intensity light emission data. Absolute light intensity units refer to light emission data from the source or sample itself. The absolute light intensity data may be represented with a variety of units. In one embodiment, the absolute light intensity units are provided in units of radiance. For example, the total signal for absolute intensity data may be represented as "total flux" (photons/sec). This refers to the radiance in each pixel summed (or integrated) over an area of interest. The quantity "area" is the region of interest area in square centimeters. The result may also be multiplied by $4\pi$ to indicate the number of photons that are radiating into a sphere. The rate of photons leaving a sphere surrounding a light source is typically called flux, hence the designation "total flux". Flux from a sphere is useful for light sources modeled as a point source such as a cell or small tumor. The average signal in photon mode may be designated "average radiance" and this is simply the sum of the radiance from each pixel inside a region of interest divided by the number of pixels in the region of interest.

In one embodiment, the quantity photons/second/centimeter squared/steradian is used. The radiance units of photons/second/centimeter squared/steradian refers to the number of photons per second that are leaving a square centimeter of a light source and radiating into a solid angle of one steradian (sr). One skilled in the art has an understanding of steradians, but briefly, a steradian can be thought of as a 3-dimensional cone of light emitted from a surface that has unit solid angle, much like $cm^2$ is a unit area. For light sources that radiate isotropically into a sphere, that is defined as $4\pi$ steradians. Lens systems generally pick up only a small fraction of the total $4\pi$ steradians and the size of the cone may be determined based on the known size of the camera lens. This unit of measure is particularly useful for light sources imaged from a diffuse surface such as the exterior of a small mammal.

Another suitable unit is "watts". This is similar to "photons" described above in that the image intensity refers to surface radiance on the sample. The units of radiance in this case are watts/$cm^2$/sr. Watts is related to photons/sec by a scale factor that depends on the wavelength of detected light.

The relative intensity data produced by the camera is usually specific to the individual imaging system. Counts are uncalibrated units that refer to the amplitude of the signal detected by a digitizer incorporated into a camera. As a rough approximation, the number of counts detected by the digitizer is similar to the number of photons incident on a given pixel, but this is not an exact relationship and it can change from camera to camera. Often, the signal level in counts for each pixel is limited by the 16-bit digitizer in the range of 0-65535.

Since a signal measured in counts is related to the number of photons incident on the camera, the signal level will vary depending on camera settings such as integration time, binning, f/stop and field-of-view. Thus, if a researcher must change these settings in the middle of an experiment consisting of serial images to keep the signal below the digitizer saturation level of 65535 counts, then the image measurements should be corrected for the change in camera settings. In the case of changing the integration time, the scaling of signal is very straightforward since the signal is proportional to integration time. However, changes in f/stop or field-of-view result in changes to the signal level for which scaling is more difficult.

Figure 2A:
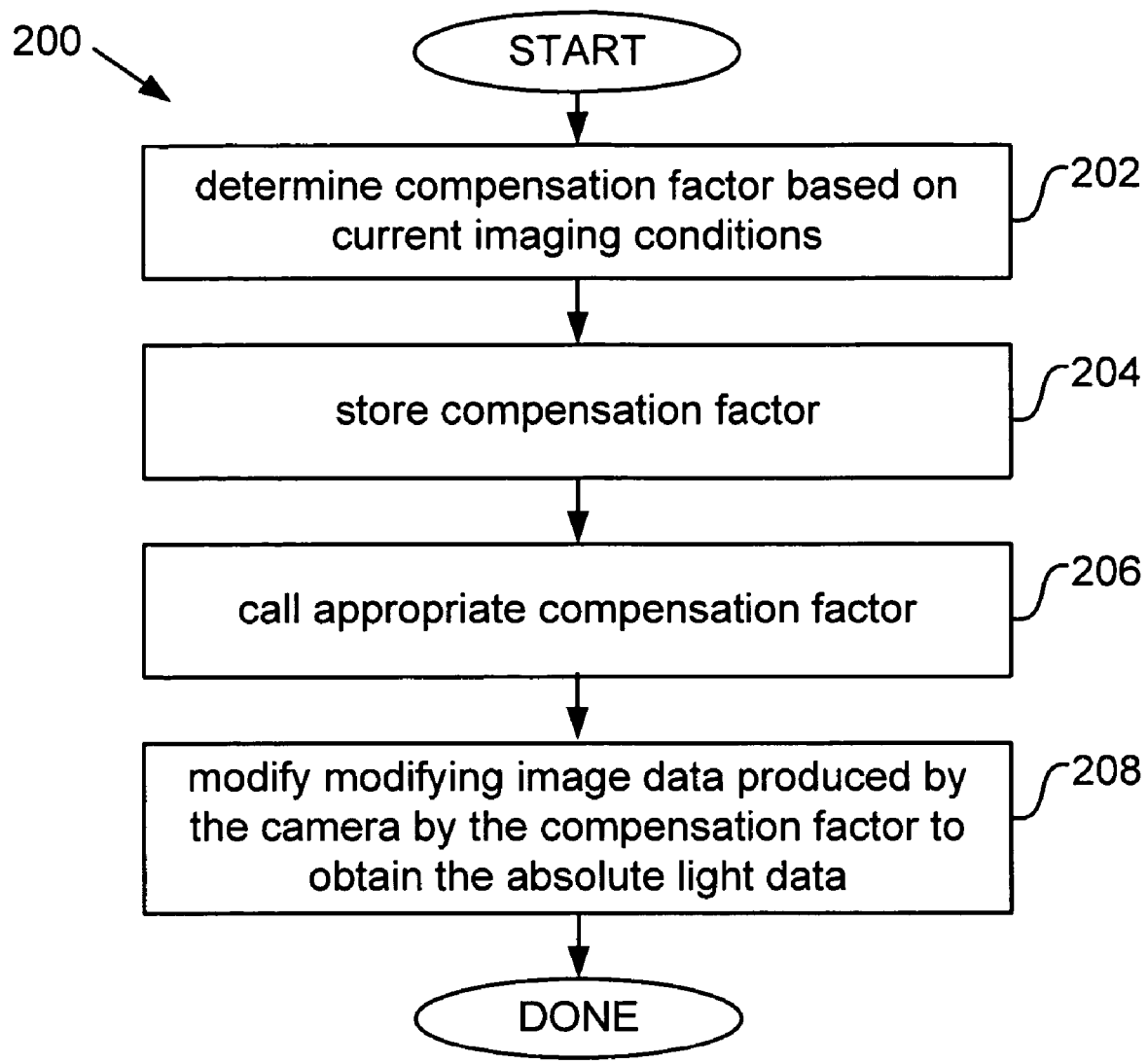
FIG. 2A illustrates a process flow for producing absolute light data for a light source being imaged at low intensity light levels in accordance with one embodiment of the present invention.

In these cases, the present invention employs a compensation factor to convert between relative intensity data produced by a camera and absolute intensity data from the light source. FIG. 2A illustrates a process flow 200 for producing absolute light intensity data using a compensation factor for a light source being imaged at low intensity light levels in accordance with one embodiment of the present invention. The low intensity light source may emit light on the order of individual photons, for example.

Process flow 200 begins with determining a compensation factor for each imaging condition in the imaging system (202). As the term is used herein, a compensation factor refers to any proportionality constant, mathematical representation or equation that converts between camera output data and light data emitted by the light source. The compensation factor typically accommodates for at least one variation between camera output and light emission by the light source resulting from hardware or other imaging system conditions that affect light transmission or light data processing. As will be described with respect to FIG. 2B, a compensation factor is determined based on assessing camera output against a known light source for a specific set of imaging conditions in the imaging system.

The compensation factor is then stored in memory (204). In one embodiment, the compensation factor is stored in a look up table that includes an entry for each imaging condition in the imaging system. For example, an imaging system with four different filter types, three different f-stop options, and eight stage positions may include 72 entries in the look up table ($4 \times 3 \times 8 = 72$), where each entry corresponds to a unique combination of filter type, f-stop option, and stage position. Obviously, a different look up table may be implemented for each imaging system based on hardware and imaging options local to a particular system. In some cases, compensation factors may be determined for subsets of the imaging conditions in the systems such that when an individual hardware type is not used or removed, compensation factors have already been determined. For example, a fifth option for the filter type might be no filter, and the look up table would be expanded accordingly to fit all cases when a filter is not used.

Upon subsequent imaging with a specific condition in the imaging system, a corresponding compensation factor is called from memory based on imaging conditions corresponding to a particular image being processed (206). The processor used to control the imaging system may then be responsible for reading the current imaging conditions and accessing the lookup table based on these conditions to obtain the appropriate compensation factor. By storing and automatically calling a compensation factor for each imaging condition in the imaging system, absolute imaging data may be obtained automatically without user input; thus creating a transparent mechanism for absolute light intensity data attainment. This is particularly advantageous to allow simplified and expedited imaging of light sources despite the presence of different hardware and complex imaging systems.

Process flow 200 then obtains the absolute light data by modifying image data produced by the camera for a particular image by the compensation factor (208). As mentioned before, the number of counts output by the camera is proportional to the number of photons incident on a given pixel, and the compensation factor is applied to the camera output data to obtain an absolute number based on the known imaging conditions.

Figure 2B:
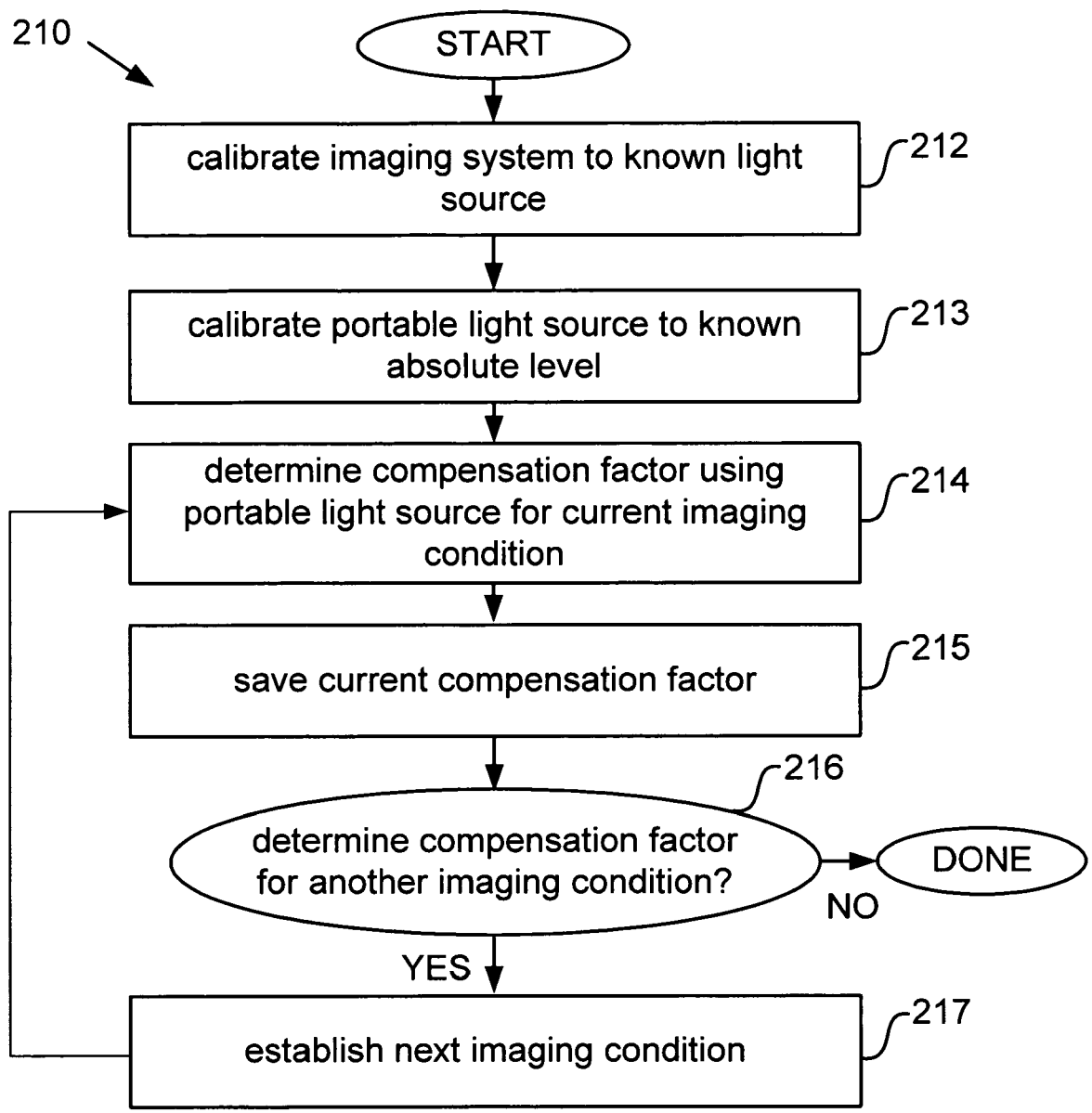
FIG. 2B illustrates a process flow for determining compensation factors in accordance with a specific embodiment of the present invention.

FIG. 2B illustrates a process flow 210 for determining compensation factors in accordance with a specific embodiment of the present invention (202 from process flow 200). A prerequisite to obtaining compensation factors in the imaging system is having a known absolute light source such that differences produced by each imaging system condition may be compared against a known emission.

Figure 4A:
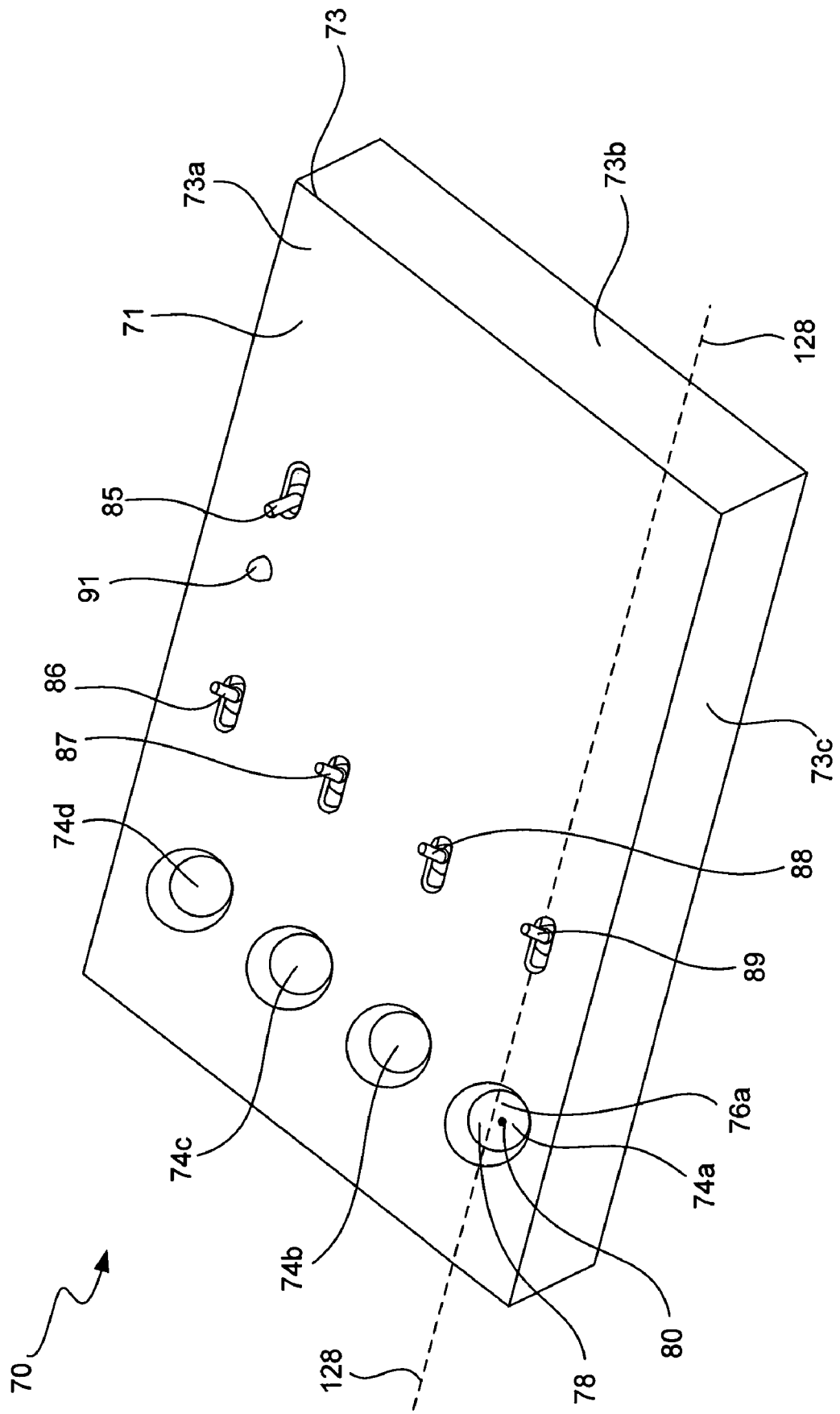
FIGS. 4A-4B illustrate different views of a light calibration device in accordance with one embodiment of the present invention.
Figure 4B:
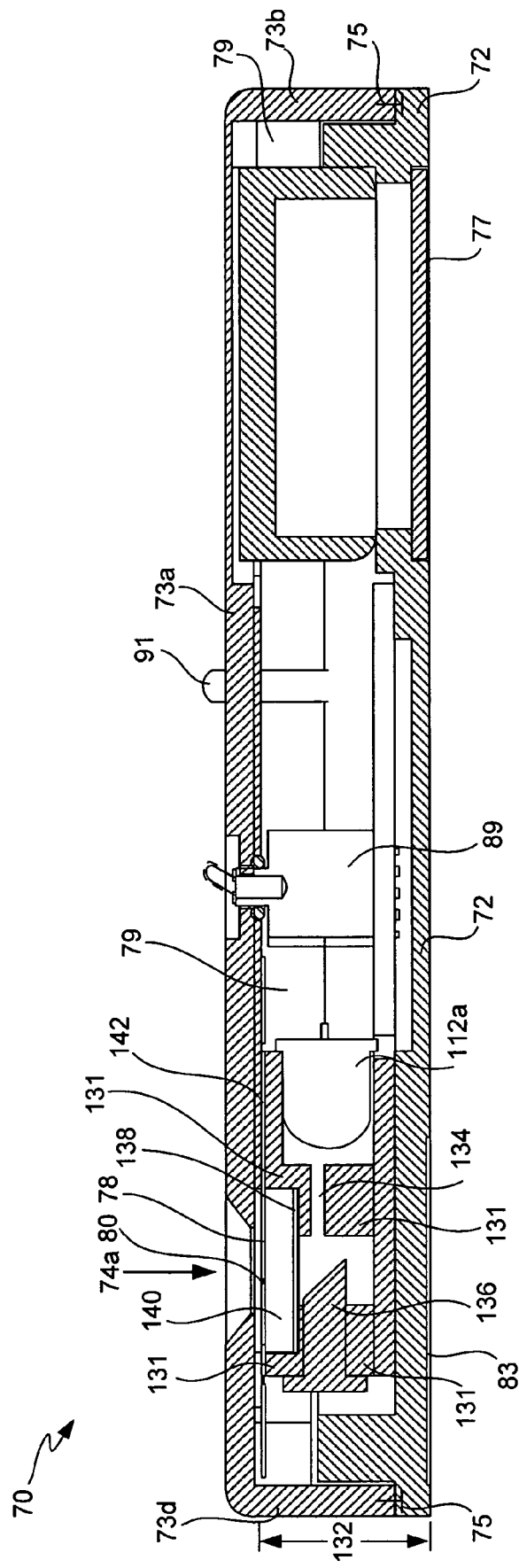
Figure 4C:
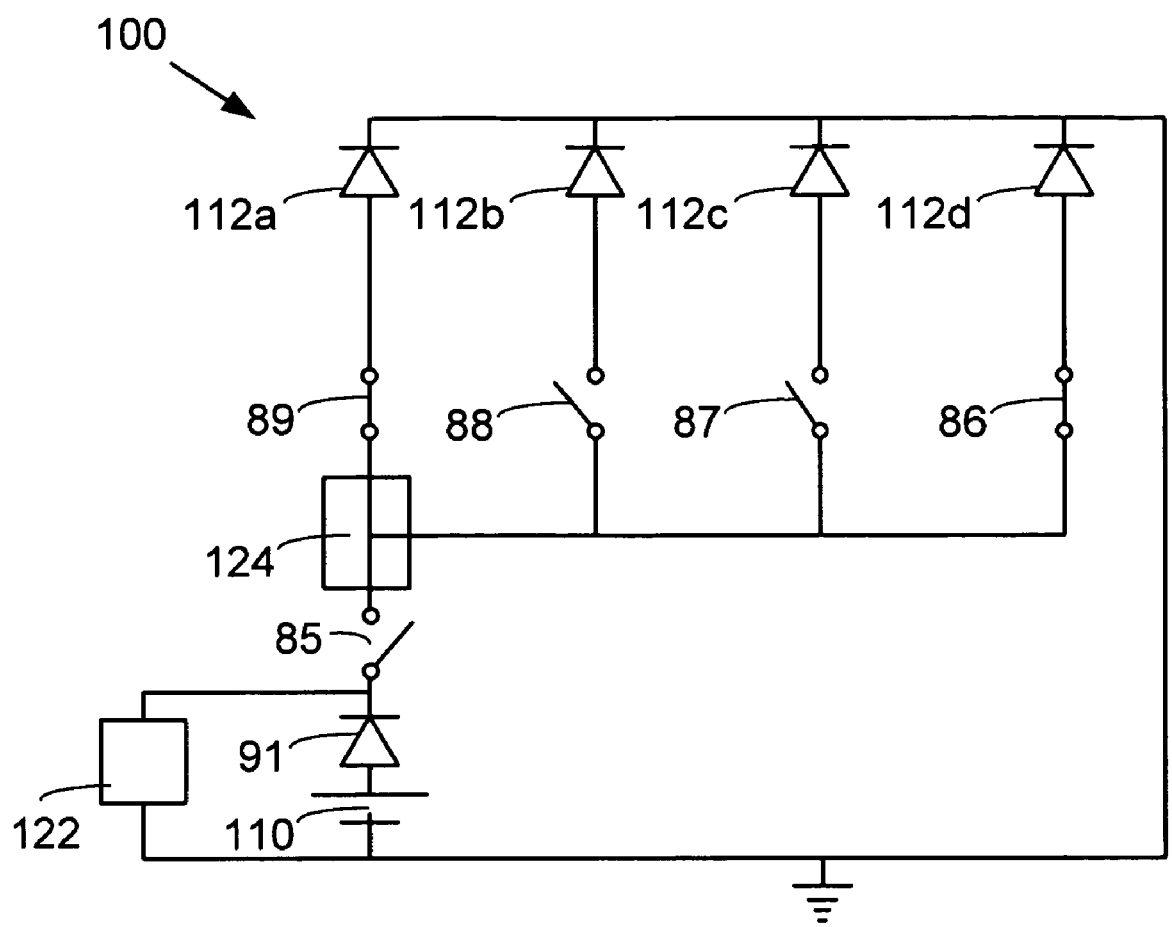
FIG. 4C illustrates an electrical schematic of the light calibration device of FIG. 4A in accordance with a specific embodiment of the present invention.

In one embodiment, process flow 210 uses a portable calibration device, such as that shown in FIGS. 4A-4C, which may be easily placed within and removed from an imaging box. The portable calibration device also allows relatively easy transportation for sale and use in imaging systems deployed in disparate facilities. Since portable calibration devices are not available at light levels typically used within imaging systems of the present invention, process flow 210 initially calibrates the portable calibration device against a known intensity light source, e.g., against a known radiance standard. For example, the light sources may be calibrated to a National Institute for Standards and Technology (NIST) traceable OL Series 425 Integrating Sphere available from Optronic Laboratories of Orlando, Fla. In one embodiment, the portable calibration device is calibrated to absolute units.

Process flow 210 uses imaging system 10 to cross calibrate the portable calibration device with the known radiance standard. Process flow 210 thus begins by inserting a device with a known radiance, such as the 425 Integrating Sphere mentioned above, within an imaging system such as imaging system 10 (212). This is done to calibrate the imaging system to known or absolute levels for a particular imaging condition suitable for calibrating the portable device, and may include calculating preliminary compensation factors from analog to digital units (or counts) as received by the camera to absolute radiance units corresponding to the emission from the known source.

Once the imaging system has been calibrated to known levels, it may be used to calibrate the portable calibration device (213). This comprises inserted device 70 into the imaging box and determining the fluence for each light source in the portable calibration device. The fluence for each light source may then be stored in memory and/or noted on a sticker included on the portable device to provide the light calibration information for each light supply in the portable calibration device. For example, the information may include absolute photon emission over time, e.g., the number of photons per second, for each light supply in the portable calibration device. The calibration of a portable calibration device may occur in a variety of ways and the present invention is not limited to how an absolute light source is obtained to determine compensation factors within the imaging system. For example, it is not necessary to use a portable calibration device as described above, and compensation factors may be determined directly using a known radiance standard.

Process flow 210 then proceeds by using the portable calibration device to determine compensation factors for various imaging conditions within the imaging box (214 to 217). This includes placing the light calibration device in an imaging box. It is important to note that this may occur at a different location and time from that used to calibrate the portable calibration device. In other words, calibration of multiple portable calibration devices may occur at a common location while each portable calibration device may be provided to individual facilities that determine compensation factors for their individual systems at a time and location unrelated to the portable calibration device calibration. In one embodiment, the portable light calibration device includes an array of low intensity light supplies. Each low intensity light supply may be illuminated using a suitable electrical switch in conjunction with a light source operably coupled to one or more of the low intensity light supplies.

A camera receives the light emitted from the calibration device and provides a signal representative of the emitted light to an associated image processing system. This may include photographic and/or luminescent image capture, and may include steps for each as described above with image capture of a sample in process flow 220. The image processing system processes the light emission data and compares the processed light data with known light emission for device. Thus, a compensation factor is determined for the current imaging conditions using the portable calibration device (214). In one embodiment, processing the light emitted from the calibration device comprises integrating the amount of light in photons received over time. Since the device may be designed to emit a known value for light per unit time produced from each light supply, a comparison of the number of photons received by the imaging system with the number of photons produced from the calibration device gives a relatively simple comparison for assessing imaging system accuracy based on the current imaging conditions. A compensation factor may then be created based on this comparison.

The compensation factor is then stored in memory based on the current imaging conditions (215). As mentioned above, the compensation factor may be stored in a look up table that includes an entry for each imaging condition in the system.

Process flow 210 then continues to determine a compensation factor for each desired imaging condition (216). In one embodiment, this includes each possible combination of hardware and configuration option included in the imaging system, several examples of which are provided below. Typically, conditions are changed one at a time and a new compensation factor is determined and stored for the new condition set one at a time. Hardware and software within the imaging system is then manipulated to achieve a desired imaging condition, according to the next compensation factor to be determined. In one embodiment, the compensation factors are all determined using a constant wavelength of light, e.g., from 600-700 nm. Imaging may then occur at any visible light wavelength from 300-700 nm or near infrared extending up to 2000 nm. In another embodiment, the compensation factors are all determined using a constant wavelength of light from about 300-1100 nm.

Compensation factor determination and storage according to process flow 210 may be flexibly applied. In some cases, process flow 210 is repeated periodically over the operational life of the imaging system, e.g., once every couple of months, to verify the operational integrity of the imaging system and its constituent hardware components over time. Alternately, the process may be repeated when new hardware such as a new camera is installed in the system.

In another embodiment, the calibration device is additionally used to assess the ability of the imaging box to seal light. In this case, light is received and processed from the low intensity light supplies for an extended period of time, long enough to assess the light integrity of the imaging box. For example, light received in the range of about 1 second to about 5 minutes may be suitable for some imaging boxes.

Generally speaking, the present invention may include determining a compensation factor for any light capture hardware, components and/or conditions of an imaging system that affect camera output. Hardware that affects camera output may include the camera, imaging box, an amplifier used in the camera, the inherent camera performance characteristics, the camera lens, an iris f-stop, any light interference filters, a window that separates the camera from the imaging box interior, the location of the sample/stage the sample is supported on, etc.

Some of these hardware components may have one or more operational conditions as determined by a user. Conditions associated with image capture using a camera that affect camera output include the spatial and spectral characteristics of the camera, and the open/close condition on an f-stop for the camera, for example. Compensation factors may be developed for any of these conditions. Field of view for a camera is a condition that may be set by the user based on desired viewing positions within the imaging system. Imaging may subsequently occur at these positions and compensation factors stored in advance for each position. In addition, intermediate positions between stored positions may be used in imaging where the difference is accounted for by interpolation between known compensation factors. Integration time may also be varied to obtain varying levels of light emission from the light source. In the case of changing the integration time, the scaling of camera output is straightforward since the signal is proportional to integration time. Binning may be implemented to account for insufficient information per pixel. More specifically, the number of pixels in each direction of the luminescence representation may be halved to produce a new pixel array comprising the magnitude of four previous pixels in a single new pixel to improve statistical analysis. Again, the scaling of camera output is straightforward since the signal is proportional to the square of binning level.

Figure 2C:
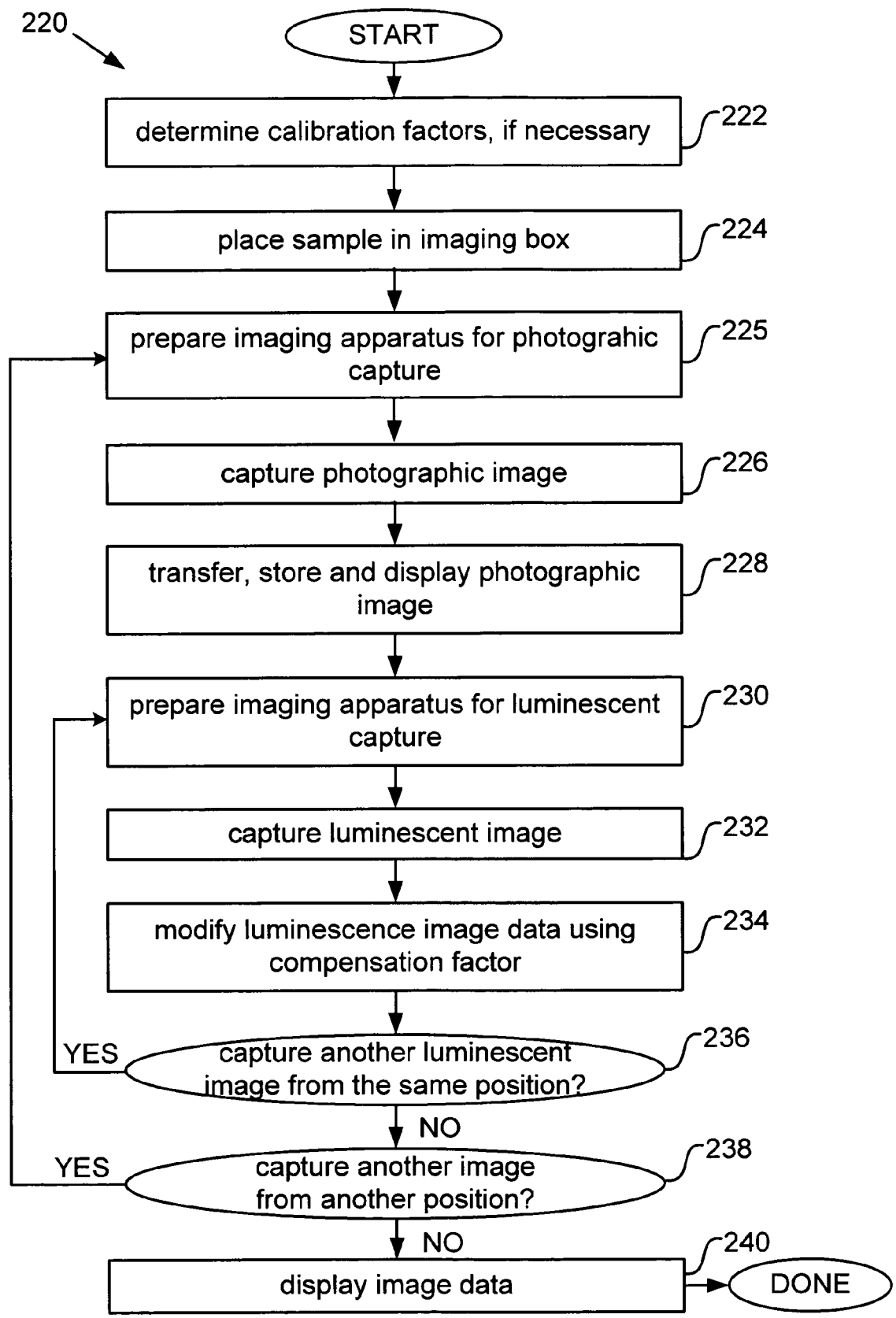
FIG. 2C is a process flow illustrating a method of capturing photographic and luminescence images using the imaging apparatus of FIG. 1 in accordance with one embodiment of the present invention.

Turning now to FIG. 2C, a process flow 220 illustrates a method of using imaging system 10 of FIG. 1 in accordance with one embodiment of the invention. If not previously performed, process flow 220 begins by placing a calibration device in an imaging box imaging box. The calibration device, imaging box and its associated imaging components are then used to determine compensation factors for the various combinations of light capture conditions and components of the imaging system (222 and FIG. 2B).

After calibration and removal of the calibration device, a sample or specimen may be placed on a stage in imaging box 12 (224). Imaging box 12 and associated image components may then be prepared for specific photographic image capture conditions (225). The preparation may include launching imaging and acquisition software (e.g., "LivingImage", Xenogen Corporation, Alameda, Calif.) on the computer 28 and initializing the camera 20. Further preparations may include selecting a desired stage position is a moveable stage is used, closing the door to box 12, activating the photographic capture option in the software, and turning on the lights in the box. Preparations may further include focusing the lens, selectively positioning an appropriate lens filter, setting the f-stop, etc. Each of these conditions is noted by computer 28.

The photographic image is then captured (226). In one embodiment, a "live mode" is used during photographic imaging of the sample to observe the sample in real time. The live mode includes a sequence of photographic images taken frequently enough to simulate live video. Upon completion of photographic capture, the photographic image data are transferred to an image processing unit 26 and/or computer 28 (228). These may be used to manipulate and store the photographic image data as well as process the data for display on computer monitor 38. In some cases, the photographic image data may be altered by a compensation factor stored and called from memory.

Subsequently, imaging box 12 and associated image components are prepared for specific luminescence image capture conditions (230). Such preparation may include, for example, selecting luminescent exposure time and binning level using the computer 28, and turning off the lights in the cavity 44. The CCD camera 20 then captures (232) the luminescence image over a set period of time (up to several minutes). The luminescence image data are transferred to the image processing unit 26 and/or computer 28, which may be used to manipulate the luminescence image data. At this point, the luminescence image data is modified by the stored compensation factor corresponding to the current imaging conditions to convert the relative output produced by the camera to an absolute light data (234). In one embodiment, the camera output is multiplied by the compensation factor to achieve the absolute light intensity data. For example, the compensation factor may be stored as a function of the absolute unit/ (count*time). Since the camera outputs counts over a duration of time, conversion to absolute units is then a simple multiplication.

Process flow 220 may include taking multiple luminescence representations from the same position of stage 204, e.g., at the same time or a later time (236). If a moveable stage is used in the imaging system, the stage may then be moved to another position (238). While the stage is at the second position, one or more photographic and/or luminescence images of the sample may be captured as described above. Upon completion of each image capture, a processor in computer 28 then receives the image data and modifies camera output to produce absolute light intensity data.

Computer 28 may also store the absolute image data, the relative image data, and imaging conditions, as well as process it for display on the computer display 38 (240). Presentation of the data may also include overlaying the luminescent image with the photographic image and displaying the two images together as an "overlay" image, with the luminescence data typically shown in pseudocolor to show intensity. At this point, the user has the components of a digital overlay image (including the luminescence image and the photographic image) stored in the computer 28. The information contained in these image may be analyzed and manipulated as desired.

The photographic and luminescence representations provided by the imaging apparatus 100 and imaging interface of the present invention have a wide variety of applications. In one particular embodiment, the luminescence representation indicates the radiance from the sample. In other words, the luminescence representation may display magnitude values for light emissions form the surface of the animal. Regions of the object emitting radiation (e.g., photons) will appear in the luminescence representation. The luminescence images may indicate the presence of a biocompatible entity, for example. The entity can be a molecule, macromoloecule, cell, microorganism, a particle or the like. Thus, an in-vivo analysis may include detecting localization of a biocompatible entity in a mammalian subject. Alternatively, the information in the live mode may be used to track the localization of the entity over time. For more examples of analysis applications for a digital overlay image suitable for use with the present invention, the reader is referred to in U.S. Pat. No. 5,650,135, which was previously incorporated by reference.

Obtaining an absolute performance of an imaging system according to the present invention is particularly useful, for example, for normalizing imaging data received from a sample. Accordingly, if a user were to take several images (during a single session) of an sample with different integration times or different fields-of-view, the displayed images would all have the same signal amplitude because the radiance on the surface of the animal is not changing—only the camera settings are changing. Basically, the camera settings have been factored out. The advantage to the user is that camera settings can now be changed during the course of an experiment and there is no need to make any adjustments to the images or the measured image data. The other advantage of absolute physical units is that images or image data can now be compared quantitatively between different camera systems at, possibly, different facilities.

One example of how absolute light intensity data can be used is the case of measuring the brightness of a luciferase tagged cell line. After imaging a well plate, image data may be collected and analyzed for an individual well. The total flux (photons/sec) emitted from a particular well may be obtained, e.g., by designating a region of interest (ROI) around an individual well using a graphical user interface. If n cells in a well plate are imaged, the total flux from a well plate may be divided by the number of cells (n), and the number of photons/sec radiating isotropically from each cell may be obtained. This is a useful number to have for each cell line so that the absolute brightness of every cell line may be assessed.

Another advantage to storing raw image data output by the camera and any compensation factors associated with the data is that the user may subsequently choose and change the units used in presenting the data. In a computer application, there are numerous ways to present and manipulate information. Graphical user interfaces on a computer system allow easy use of windows, control icons, etc. to display and manipulate information.

In accordance with one embodiment of the present invention, a graphical user interface (GUI) is provided which allows the user to perform numerous operations suitable for absolute light intensity data analysis within a single window. The graphical user interface includes automatic presentation of image data in various relative and absolute units, as desired by a user. Using the GUI of this invention, the user may create and manipulate analysis tools and perform a wide variety of measurements on complex images (such as in-vivo images) conveniently and efficiently, and in relative and absolute units of radiance—regardless of image capture hardware configuration.

Figure 3:
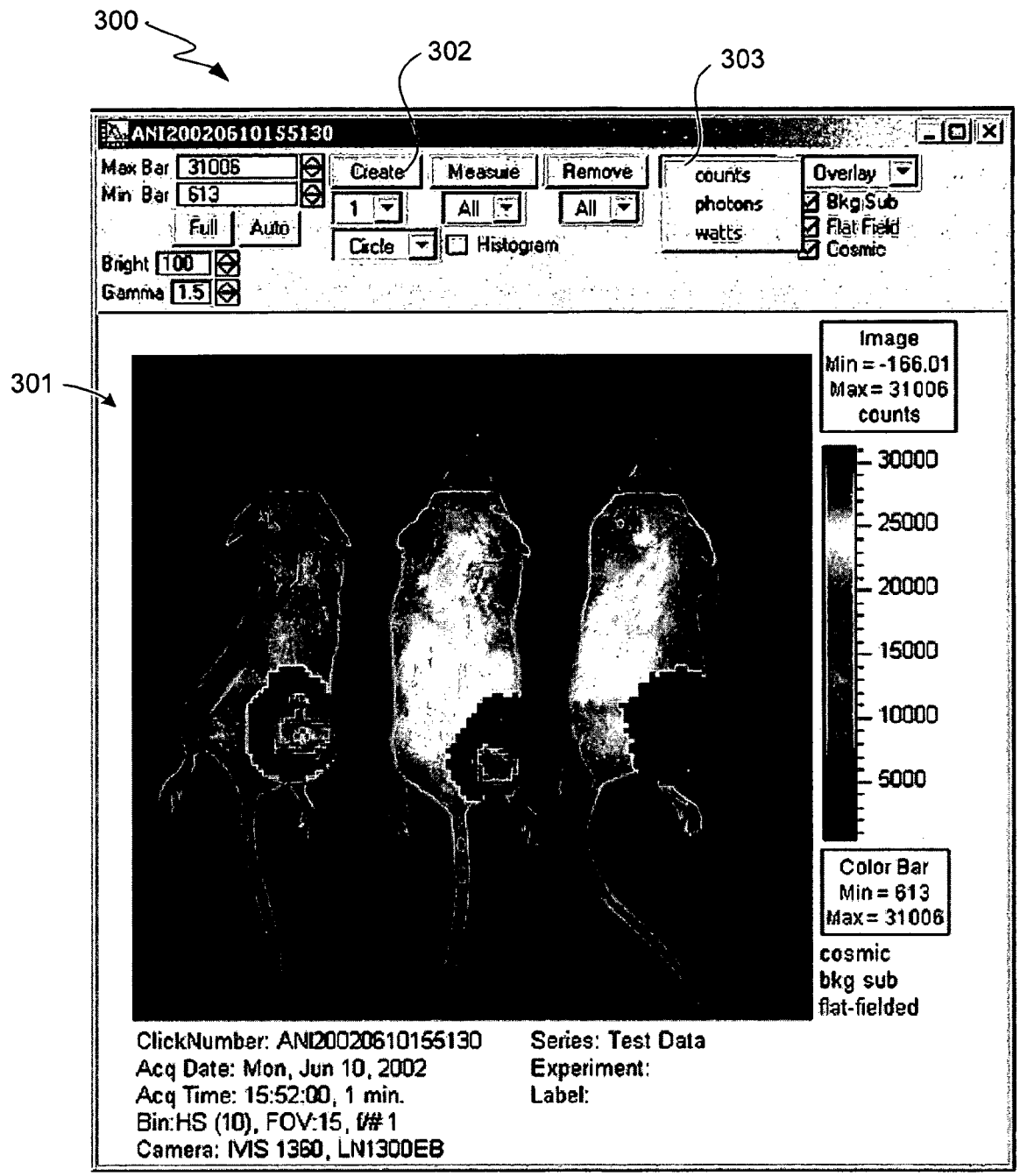
FIG. 3 illustrates one example of an image control/measurement window that visually provides data in absolute units to a viewer in accordance with this invention.

FIG. 3 illustrates one example of an image control/measurement window 300 that optionally provides data in absolute units in accordance with this invention. The image control window includes an image measurement window 301. Within the image measurement window 301, an overlay image is displayed. The overlay image includes a visual superposition of a photographic representation of the specimen and a luminescence representation of the specimen. The photographic representation provides the user with a visual frame of reference of the image. The luminescence representation provides photon emission data derived from the object. Because the imaging apparatus is typically used to measure the entire specimen, the data in the luminescence representation typically has one or more distinct luminescent portions of interest. Image control window 301 is well suited for manipulating the display of the overlay image as well as making measurements and analyzing the luminescence representation. One suitable image control window is provided in the Living Image® system as provided by Xenogen Corp of Alameda, Calif. For further description of the image control window 300, the reader is referred to in U.S. patent Ser. No. 09/439,381, which is incorporated by reference herein for all purposes.

The create function section 302 includes controls for allowing the user to create and manipulate tools which enable simple and flexible analysis of the data within the image measurement window. For example, the user simply clicks on button with a pointer and a new ROI appears in the image measurement window. The ROI may be any geometric shape or tool for measuring and analyzing data in a portion or portions of the luminescence representation.

Image control window 301 allows a user to display and analyze image data in physical units. The units window 303 allows a user to select what units are used to present the luminescent data. In a specific embodiment, three sets of units available: "counts", "photons", and "watts". When the units menu is switched to "photons", the units on the displayed image change to photons/second/centimeter squared/steradian. These are units of photon radiance on the surface of the animal. As a result, the measurements in units of radiance displayed in window 301 have taken into account settings such as integration time, binning, f/stop, and field-of-view. When displaying data in a counts mode, various count quantities may be displayed such as the quantity "total counts", which refers to the sum of all counts for all pixels inside the image, or a particular portion of the image, such as a region of interest. An average counts is the total counts divided by the number of binned pixels. The quantity "ROI Pixels" is the number of binned pixels inside the ROI while "Area (CCD pixels)" is the number of unbinned CCD pixels inside the ROI.

For image acquisition, a user may operate in units of "counts". This enables the user to adjust camera settings to optimize the signal level within the range allowed by the digitizer. This signal should be well above the noise floor of ~5 counts (>100 counts if possible) and below the saturation value of 65535 counts. For quantification of the images using measurements within a region of interest, using absolute units of "photons" may be more desirable as discussed above.

Portable Calibration Device

In one embodiment, the present invention employs a portable calibration device to assist calibration of a low level light imaging system. FIGS. 4A-4C illustrate a light calibration device 70 in accordance with one embodiment of the present invention. Calibration device 70 includes an array of low intensity light supplies 74a-d held by a housing 71.

Referring to FIGS. 4A and 4B, housing 71 provides mechanical integrity for device 70 and protects electronic components contained therein. In a specific embodiment, housing 71 comprises two pieces of machined aluminum fixed together. The first piece, containment piece 73, comprises a top 73a and four sidewalls 73b-73e which form an interior cavity 79 (FIG. 4B) in which electronic components are contained. In the embodiment where housing 71 comprises machined aluminum pieces, containment piece 73 is machined from a single block of black anodized aluminum to form sidewalls 73b-73e and top 73a, which define interior cavity 79. A matching faceplate 72 (FIG. 4B) mates with the bottom walls of containment piece 73 such that the device 70 is substantially "light-tight", e.g., it prevents essentially all of the light produced within the interior 79 from escaping housing 71 other than through the array of low intensity light supplies 74. To facilitate the light-tight nature of device 70, one or more gaskets or seals may be disposed at the mating interface of containment piece 73 and faceplate 72. For example, the gasket may comprises a sheet of adhesive backed neoprene rubber with peel off paper backing cut to size of the mating interface and cut to accommodate holes for each light source. Screws 75 detachably fix faceplate 72 to containment piece 73. Faceplate 72 also comprises a removable battery hatch 77 that allows a user access to a battery cavity within device 70. Sticker 83 is attached to faceplate 72 and provides light calibration information for each light supply 74. For example, the information may include absolute photon emission over time, e.g. the number of photons per second, for each light supply 74.

Each light supply 74 emits consistent and low-intensity light from device 70. The allowable range for light emitted from each light supply 74a-74d will depend on a number of factors such as the sensitivity and saturation of the camera used, the ability of the imaging box to seal light, level of internally generated light in the imaging box, imaging system parameters such as integration time, binning, and f-stop, etc. In one embodiment, the intensity of light emitted from a light supply 74 may be determined according to the sensitivity of a camera used in the imaging system over a duration corresponding to saturation of the camera caused by light emitted from the light supply 74. Saturation refers to the amount of light and time it takes for the camera, or the analog-to-digital converter associated with the camera, to reach its exposure capacity. For example, the saturation duration may range from about five seconds to about five minutes, depending on the rate of light emitted from the object.

Each light supply 74 comprises a light source that generates light. In one embodiment, the array of light supplies 74 is 'discrete' in that each light supply 74 receives light from a single light source dedicated to an individual light supply. Since most conventional light sources produce too much light and may saturate a low-level light imaging system, the light produced from the light source may be reduced in intensity before emission from each light supply 74. To reduce the intensity of light produced from each light source and to control the light emitted from device 70, each light supply 74 comprises a light interface 76 for receiving light from a light source and emitting at least a portion of the light from the device 70.

For example, light supply 74a comprises a light interface 76a that facilitates spatial calibration for an imaging system. Light interface 76a includes an opaque diaphragm 78 having a light transmission pinhole 80. In one embodiment, pinhole 80 has a known and tightly toleranced diameter such that light emitted from light supply 74a, received by a camera, and processed by an imaging system, produces an image whose diameter may be compared with the known diameter of pinhole 80. This may be advantageous to assess imaging system, or camera, spatial integrity for detecting the size of imaged objects. For example, spatial calibration using light supply 74a is suitable to detect the presence of any 'bleed' between channels of a camera. Pinhole 80 diameters in the range of 10 microns to about 100 microns are suitable for many applications. Alternately, pinhole 80 diameters in the range of about 30 to about 100 microns may be suitable. In a specific embodiment, diaphragm 78 is aluminum and pinhole 80 is machined using laser drilling or other suitable tightly toleranced machining techniques.

Light supply 74a is also suitable for assessing the spatial integrity between photographic and luminescent image capture for an imaging system. For example, an overlay image comprising a combination of a luminescent image of device 70 disposed overtop a photographic image of device 70 will readily indicate spatial inconsistencies of the location of pinhole 80 between the luminescent image and the photographic image. The offset may then be used to calibrate the system or alleviate the inconsistency.

Light supplies 74b-74d emit light that enables spectral calibration. More specifically, light supply 74b emits green light of a known wavelength, light supply 74c emits red light of a known wavelength and a relatively low intensity, and light supply 74d emits red light of a known wavelength and a higher intensity than that of light supply 74c. Since the spectral resolution of many CCD cameras may diminish at the borders of the visible light spectrum, light supplies 74b-74d may be used to assess the spectral integrity of the imaging system within, and at the extremes, of the visible light spectrum. Light received by a camera, and processed by an associated imaging system, may produce an image whose spectral characteristics are compared to known spectral emissions for light supplies 74b-74d.

Light supply 74c and light supply 74d emit a low intensity and high-intensity relative to each other. In a specific embodiment, light supply 74c emits light in the range of about $10^3$ to about $10^5$ photons/second/centimeter squared/steradian while light supply 74d emits light in the range of about $10^7$ to about $10^9$ photons/second/centimeter squared/steradian. Again, the amount of light emitted from each light source may vary based on a particular camera and system being calibrated.

Device 70 also comprises a series of switches 85-90. Switch 85 acts as a master on/off switch for device 70 and allows the user to turn on/off all the light supplies 74 simultaneously. Status indicator 91 indicates operation of device 70. In one embodiment, status indicator 91 temporally flashes to indicate operation of device 70 so as to not overwhelm light emitted from the low intensity light supplies 74 during calibration. A conventional off-the-shelf diode may be suitable to temporarily produce light for status indicator 91. Switches 86-89 allow separate on/off control for each light supply 74. More specifically, switch 86 allows individual on/off control of light supply 74d, switch 87 allows individual on/off control of light supply 74c, switch 88 allows individual on/off control of light supply 74b, and switch 89 allows individual on/off control of light supply 74a.

FIG. 4C illustrates an electrical schematic 100 of light calibration device 70 in accordance with a specific embodiment of the present invention. As shown, calibration device 70 includes voltage source 110, light sources 112, switches 85-89, voltage shut off 122, status indicator 91, and voltage regulator 124.

Voltage source 110 is in electrical communication with light sources 112 and provides voltage and power to electrical components employed within calibration device 70. In a specific embodiment, voltage source 110 comprises between 1 and 5 conventional AAA batteries.

Light sources 112a-d generate light. As will be described in greater detail with respect to FIG. 2B, much of the light generated by light sources 112 is not emitted from device 70, but instead is reduced in intensity to achieve low intensity light levels desirable for many specialized imaging applications. In one embodiment, light sources 112a-d each comprise a low intensity diode. A low intensity diode model number IPL1060630JAL as produced by Integrated Photomatrix of Dorchester, Dorset, England may be suitable as a light source for use within calibration device 70.

Device 70 may include electrical components to facilitate substantially consistent light output over the operating life of the calibration device. In a specific embodiment, light sources 112a-d are self-monitoring in that the light sources are designed or configured to monitor the amount of light generated therefrom and adapt the amount of light to maintain substantially consistent light output from device 70. More specifically, the output from the monitoring diode may be used to control the current flowing to the LED, in order to maintain a constant light level, irrespective of aging or temperature effects. The receiving detector may be used to give an absolute indication of transmissivity through the medium, since the light level is held constant. Using self-monitoring light sources in this manner allows device 70 to accommodate minor fluctuations in temperature or voltage without sacrificing consistent light output.

Device 70 may also include additional electrical components to facilitate substantially consistent light output over the operating life of the calibration device. For example, a voltage shut off 122 may be disposed in electrical communication with voltage source 110. Voltage shut off 122 terminates voltage provided by voltage source 110 to light sources 112a-d when the voltage provided by voltage source 110 becomes insufficient to produce allowable light output from light supplies 74, e.g., due to battery age. In addition, device 70 may include a voltage regulator 124 in electrical communication with voltage source 110. Voltage regulator 124 controls the voltage and current provided to each light source 112.

Additional measures may further be taken to increase radiometric stability of the light sources over time. In a specific embodiment, a light source includes a self-monitoring photodiode and uses external components to monitor the diode's light output. In this manner, the light output from the diode can be held substantially constant. To further improve radiometric stability over time, a battery level sensing circuit may be employed that denies the diode a supply voltage if the battery power level may undesirably effect diode light output. In this manner, light source stability remains substantially consistent for a long period of time, e.g., months to a year.

Referring to FIG. 4B, a side perspective view of calibration device 70 is illustrated along dashed line 128 of FIG. 4A. Device 70 comprises an optic block 131 that holds the light generation and light interface components of device 70. Optic block is fixed to housing 71. As shown, FIG. 4B illustrates light supply 74a of FIG. 4A and its constituent light source 112a and light interface. In this case, the light interface for light supply 74a comprises channel 134, deflection interface 136, neutral density filter 138, diffuser 140, and several other components to reduce the amount of light emitted from device 70.

As shown in FIG. 4B, light source 112a comprises a low intensity diode disposed on its side in order to reduce the height 132 of device 70. As will be described below, the height 132 of device 70 may be limited in some cases based on the depth of field of focus of an imaging system that device 70 is employed with. Light emitted from light source 112a passes substantially horizontally through light channel 134 and strikes deflection interface 136. Deflection interface 136 deflects light emitted horizontally by light source 112a and directs a portion of the light upward for emission from device 70. In one embodiment, the surface of deflection interface 136 facing light source 112a is angled upward to increase the amount of light directed upward. Alternately, the surface of deflection interface 136 may be vertical and perpendicular to the direction of light emitted from light source 112a, thereby reducing the amount of light reflected and producing a more Lambertian reflection. Deflection interface 136 may be constructed of Teflon, for example. In another embodiment, a mirror or otherwise suitably reflective surface may be attached to deflection interface 136 to increase, or otherwise control, the amount of light transmitted from light source 112a upwards.

Disposed along a light path between light source 112a and emission of light from light supply 74a is neutral density filter 138. Thus, light transmitted upwards by deflection interface 136 passes through neutral density filter 138. Neutral density filter 138 attenuates—or reduces the intensity of—light transmitted through filter 138 across all wavelengths. In some designs, a neutral density filter 138 is disposed to control the output intensity of light emitted from each light supply 74. In a specific embodiment, neutral density filter 138 comprises a stack of 2-4 different filters. For example, a neutral density filter model number K53-706 as produced by Kodak of Rochester, N.Y. is suitable for use within calibration device 70.

Disposed along a light path between light source 112a and emission of light from light supply 74a is diffuser 140. Diffuser 140 diffuses, or otherwise affects or controls, light emitted from light supply 74a. Diffuser 140 effectively establishes light supply 74a as a surface emitter. In one embodiment, diffuser 140 converts relatively focused or directional light reflected from deflection interface 136 into substantially Lambertian light emitted from light supply 74a. In this manner, calibration using device 70 reduces dependency on the position of calibration device 70 within imaging box 12 relative to the camera. In some cases, diffuser 140 allows light emitted from device 70 to form a particular pattern. In a specific embodiment, diffuser 140 includes an opalized surface that is particularly effective for creating a Lambertian distribution. For example, a diffuser model number L46-105 as produced by Edmund Industrial Optics of Barrington, N.J. is suitable for use within calibration device 70.

Retainer 142 holds diffuser 140 to optic block 131 and is attached to the optic block 131, e.g., using screws. Retainer 142 also includes a central portion, disposed between light source 112a and emission of light from light supply 74a, that includes the opaque diaphragm 78 and pinhole 80 described above with respect to FIG. 4A. In one embodiment, the size of pinhole 80 is used to control the amount of light emitted from light supply 74. Thus, any one or more of the interface components—e.g., diffuser 140, neutral density filter 138, and pinhole 80—may be used to control the intensity of light emitted from one of the light supplies 74a-d of FIG. 4A. Since the emission characteristics of each component is known before assembly of device 70, this allows a limited set of pre-manufactured components to be flexibly selected during device 70 manufacture to obtain a custom light emission for each light supply. Component selection in this manner enables simple, flexible, and modular manufacturing techniques to produce light calibration devices with light sources each having a custom light emission.

Height 132 is defined as the distance from the bottom cover to the top of the emitting surface for each light source. In one embodiment, height 132 is configured relative to the depth of field of focus of an imaging system that the device 70 is used with. Alternately, height 132 may be designed relative to the average height of a surface of a specimen to be imaged. It is understood that the depth of field of focus for an imaging system will vary depending on several parameters, and vary with the type of imaging performed in the system (e.g., camera characteristics and continual imaging of the top surface of a mammalian specimen is then dependent on the mammal); and the height 132 of calibration device 70 may be tailored accordingly. A calibration device having a height between about 5 mm to about 30 mm is suitable for many imaging systems. In a specific embodiment, height 132 is about 15 mm, which corresponds to the average height of a mammalian specimen commonly used in imaging applications. Calibration device 70 as shown in FIG. 4B has a height 132 of about 15 mm.

While the present invention has been described with respect to a particular light source arrangement for calibration device 70, is understood that the number of light sources 74, and the frequency and intensity of light emitted from each light source, may depend on a particular application. For example, while calibration device 70 has been described with respect to four light supplies 74, is understood that calibration device 70 may include an array of light supplies ranging from 1 to 64 light supplies, as desired for calibrating a particular imaging system. For many imaging systems, 2-8 light supplies are sufficient. In one design, calibration device 70 includes four light supplies, each having a light intensity an order of magnitude larger than its neighbor. This design is particularly advantageous to compare the sensitivity of different imaging systems. More specifically, a low quality imaging system may only be able to detect the fourth light supply having the largest intensity while a high quality imaging system will be able to detect all four light supplies. Alternately, calibration device 70 may comprise four light supplies each having a different spectral frequency. For example, four conventional light emitting diodes each having an emission frequency in between 425 and 950 nanometers may be used. This design is particularly well-suited to calibrate and assess the spectral characteristics and integrity of an imaging system.

In one embodiment, calibration device 70 includes a linear array of light supplies 74 that extend the focal radius of a camera. Calibration using this device is particularly well-suited to measure flat field correction of a camera. Flat field correction of a camera refers to calibration corrections factored into imaging due to camera lens curvature at the lens periphery. In this case, the linear array may comprise 16 light supplies that span the radius of a camera lens, for example.

Alternative Calibration Devices

Figure 5:
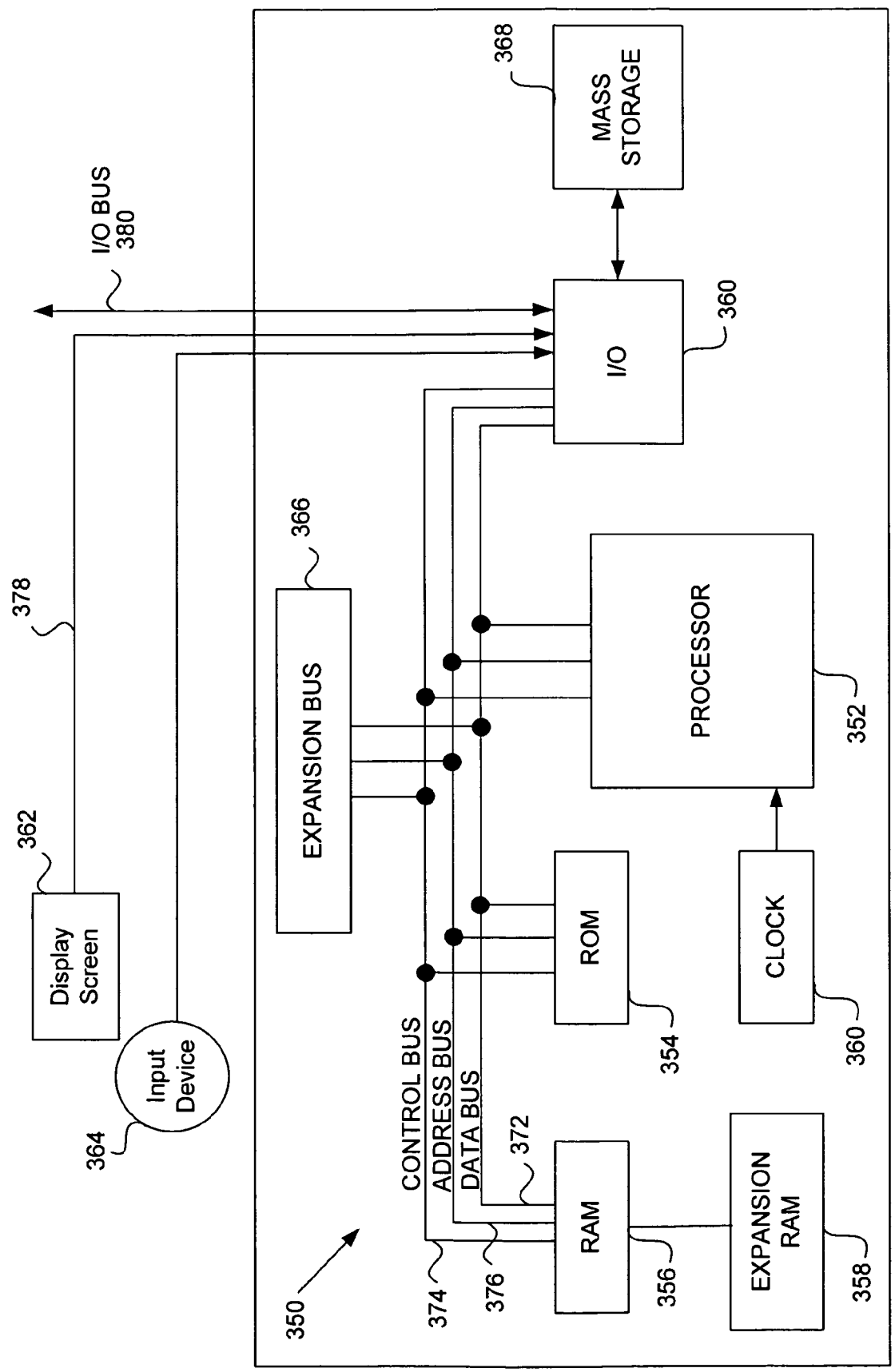
FIG. 5 illustrates a computer system suitable for implementing embodiments of the present invention.

The compensation techniques of the present invention will typically be implemented by a suitable processor or computer-based apparatus. Referring to FIG. 5, an exemplary computer system 350 includes a central processing unit (CPU) 352, read only memory (ROM) 354, random access memory (RAM) 356, expansion RAM 358, input/output (I/O) circuitry 360, display assembly 362, input device 364, and expansion bus 366. Computer system 350 may also optionally include a mass storage unit 368 such as a disk drive unit or nonvolatile memory such as flash memory and a real-time clock 360. In one embodiment, mass storage unit 368 may include units which utilizes removable computer readable media, such as floppy disks, opto-magnetic media, optical media, and the like for the storage of programs and data.

CPU 352 is a commercially available microprocessor such as one of the Intel (including Pentium™) or Motorola family of chips, a reduced instruction set computer (RISC) chip such as the PowerPC™ microprocessor available from Motorola, Inc, or any other suitable processor. CPU 352 is coupled to ROM 354 by a data bus 372, control bus 374, and address bus 376. ROM 354 may partially contain the basic operating system for the computer system 350. CPU 352 is also connected to RAM 356 by busses 372, 374, and 376 to permit the use of RAM 356 as scratch pad memory. Expansion RAM 358 is optionally coupled to RAM 356 for use by CPU 352. CPU 352 is also coupled to the I/O circuitry 360 by data bus 372, control bus 374, and address bus 376 to permit data transfers with peripheral devices.

I/O circuitry 360 typically includes a number of latches, registers and direct memory access (DMA) controllers. The purpose of I/O circuitry 360 is to provide an interface between CPU 352 and such peripheral devices as display assembly 362, input device 364, mass storage 368, and/or any other I/O devices included in the imaging system. I/O circuitry 360 may also include analog-to-digital (A/D) converters, digital-to-analog (D/A) converters, as well as other control circuits for controlling and receiving feedback data from the I/O devices. Display assembly 362 of computer system 350 is an output device for displaying objects and other visual representations of data.

The screen for display assembly 362 can be a device that uses a cathode-ray tube (CRT), liquid crystal display (LCD), or the like, of the types commercially available from a variety of manufacturers. Input device 364 can be a keyboard, a mouse, a stylus working in cooperation with a position-sensing display, or the like.

Some type of mass storage 368 is generally considered desirable. However, mass storage 368 can be eliminated by providing a sufficient amount of RAM 356 and expansion RAM 358 to store user application programs and data. In that case, RAMs 356 and 358 can optionally be provided with a backup battery to prevent the loss of data even when computer system 350 is turned off. However, it is generally desirable to have some type of long term mass storage 368 such as a commercially available hard disk drive, nonvolatile memory such as flash memory, battery backed RAM, PC-data cards, or the like.

Regardless of computer system 350 configuration, it may employ one or more memories or memory modules configured to store program instructions for modifying data output by a camera and other functions of the present invention described herein. Such memory or memories may also be configured to store data structures such as a look up table including all the compensation factors, imaging data, or other specific non-program information described herein.

Because such information and program instructions may be employed to implement the systems/methods described herein, the present invention relates to machine-readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave travelling over an appropriate medium such as airwaves, optical lines, electric lines, etc. Examples of program instructions include both machine code, such as produced by a compiler, and files containing higher level code that may be executed by the computer using an interpreter.

It should be borne in mind that although computer system 350 is discussed in some detail herein to facilitate discussion, the invention may be practiced using a variety of suitable computer-implemented techniques. In general, any suitable computer system may be employed for obtaining a three-dimensional representation of a light source located inside a sample. Further, the inventive reconstruction techniques disclosed herein may be implemented via a computer network, such as a local area network (LAN), wide area network (WAN) or a global computer network such as the Internet. In the latter cases, the reconstruction techniques may be implemented at least in part as downloadable computer software and data (e.g., applets such as JAVA™ applets from Sun Microsystems Inc.). The downloadable computer software and data may be kept on one or more servers on the network, accessible by any client computer or terminal capable and authorized for such access. Network computing techniques and implementations are well known in the art and are not discussed in great detail here for brevity's sake.

While this invention has been described in terms of several preferred embodiments, there are alterations, permutations, and equivalents which fall within the scope of this invention which have been omitted for brevity's sake. For example, although the light supplies 74 are illustrated and described each with a dedicated light source, it is understood that multiple light supplied may share a light source. It is therefore intended that the scope of the invention should be determined with reference to the appended claims.

What is claimed is:

1. A method for generating absolute fluorescent light intensity data for a fluorescent light source being imaged at low intensity light levels, the method comprising:
    determining a compensation factor for converting data output by a camera into absolute fluorescent intensity light data, the compensation factor corresponding to a set of imaging conditions;
    storing the compensation factor;
    calling the compensation factor based on the set of imaging conditions when the set of imaging conditions are used in imaging the fluorescent light source; and
    modifying image data, output by the camera, by the compensation factor to obtain the absolute fluorescent light intensity data for the fluorescent light source, wherein the fluorescent light source emits light with an intensity in the range of about $10^3$ to about $10^{10}$ photons/second/centimeter squared/steradian, and wherein the fluorescent light source includes fluorescing molecules.

2. The method of claim 1 wherein the fluorescing molecules are included in a mammal.

3. The method of claim 2 wherein the mammal is a mouse.

4. The method of claim 1 wherein the fluorescing molecules are included in one of: a tissue culture plate, a multi-well plate, and a plant containing light-emitting fluorescent molecules.

5. The method of claim 1 further comprising capturing an image of the fluorescent light source using the camera.

6. The method of claim 1 further comprising placing a portable light calibration device in the imaging box, the light calibration device including an array of low intensity light supplies.

7. The method of claim 6 further comprising receiving the light from the one or more of the low intensity light supplies using the camera.

8. The method of claim 7 wherein determining the compensation factor comprises comparing the light received by the camera with a known light emission for the one or more of the low intensity light supplies.

9. The method of claim 1 wherein the compensation factor is stored in a look up table.

10. The method of claim 9 wherein the compensation factor is stored in the look up table according to the set of imaging conditions.

11. The method of claim 1 wherein the absolute fluorescent light data is expressed in physical units.

12. The method of claim 11 wherein the absolute fluorescent light data is expressed in radiance.

13. The method of claim 1 wherein the compensation factor accommodates for a hardware structure that produces a difference between the amount of light emitted by the fluorescent light source and data output by the camera.

14. The method of claim 13 wherein the compensation factor accommodates for a difference resulting from one of: a lens disposed between the source and the camera, an f-stop associated with the camera, an iris associated with the camera, and a window disposed between the source and the camera.

15. A method for imaging a light source at low intensity light levels in an imaging system including a camera and an imaging box, the method comprising:
    placing a portable light calibration device in the imaging box, said portable light calibration device having been calibrated against a known absolute intensity light source;
    setting one or more image capture conditions in the imaging system;
    determining a compensation factor that accommodates for differences between light emitted from the portable light calibration device and data output by the camera based on said one or more image capture conditions;
    removing said portable light calibration device from the imaging box;
    placing a light source which is to be imaged in the imaging box;
    capturing image data from the light source using the camera; and
    converting image data produced by the camera to absolute light intensity data for the light source using said compensation factor.

16. The method of claim 15 wherein the absolute intensity data includes an intensity in the range of about $10^3$ to about $10^{10}$ photons/second/centimeter squared/steradian.

17. The method of claim 15 further comprising:
    storing the compensation factor.

18. The method of claim 17 wherein the compensation factor accommodates for a hardware structure that produces a difference between the amount of light emitted by the light source and data output by the camera.

19. A computer readable medium including instructions for generating absolute light intensity data for a fluorescent light source being imaged at low intensity light levels in an imaging box, the instructions comprising:
    instructions for determining a compensation factor for convening relative intensity data output by a camera into absolute light data, the compensation factor corresponding to differences between light emitted from a portable light calibration device and data output by the camera for a set of imaging conditions within the imaging box;
    instructions for storing the compensation factor;
    instructions for calling the compensation factor based on the set of imaging conditions when the set of imaging conditions are used in imaging the light source within the imaging box; and
    instructions for modifying image data, output by the camera, by the compensation factor to obtain the absolute light intensity data for the light source.

* * * * *

UNITED STATES PATENT AND TRADEMARK OFFICE
CERTIFICATE OF CORRECTION

PATENT NO. : 7,663,664 B2 Page 1 of 1
APPLICATION NO. : 11/523480
DATED : February 16, 2010
INVENTOR(S) : Rice et al.

It is certified that error appears in the above-identified patent and that said Letters Patent is hereby corrected as shown below:

Title Page, insert:
--Related U.S. Application Data
(63) Continuation of application No. 10/177,647, filed on Jun. 20, 2002, now Pat. No. 7,116,354, which is a continuation-in-part of application No. 10/068,573, filed on Feb. 6, 2002, now Pat. No. 6,919,919.

(60) Provisional application No. 60/299,685, filed Jun. 20, 2001.--.

In the Specification:
Col. 2, line 4, change "In View" to --In view--.

Signed and Sealed this

Eighteenth Day of May, 2010

David J. Kappos
*Director of the United States Patent and Trademark Office*